United States Patent [19]

Rösner et al.

[11] Patent Number: 5,723,461
[45] Date of Patent: Mar. 3, 1998

[54] QUINOXALINES, A PROCESS FOR THEIR PREPARATION AND THEIR USE

[75] Inventors: Manfred Rösner, Eppstein, Germany; Uta-Maria Billhardt-Troughton, Raleigh, N.C.; Reinhard Kirsch, Braunschweig, Germany; Jörg-Peter Kleim, Kelkheim, Germany; Christoph Meichsner, Liederbach, Germany; Günther Riess, Hattersheim, Germany; Irvin Winkler, Liederbach, Germany

[73] Assignee: Hoechst Aktiengesellschaft, Frankfurt am Main, Germany

[21] Appl. No.: 544,290

[22] Filed: Oct. 17, 1995

[30] Foreign Application Priority Data

Oct. 21, 1994 [DE] Germany .................. 44 37 406.2

[51] Int. Cl.$^6$ ................ A61K 31/495; C07D 241/44
[52] U.S. Cl. ............................ 514/249; 544/354
[58] Field of Search ............. 514/249; 544/354

[56] References Cited

FOREIGN PATENT DOCUMENTS 0 509 398 A1  10/1992  European Pat. Off. .
0 657 166 A1  6/1995   European Pat. Off. .

OTHER PUBLICATIONS

Robert Ning et al., Quinazolines and 1,4-benzodiazepines. XLVI. Photochemistry of nitrones and oxaziridines, J. Heterocycl. Chem. (1970), 7(3), 475–8.
R. Ian Fryer et al., Synthesis of amidines from cyclic amides, J. Org. Chem. (1969), 34 (4), 1143–5.
A. Mederos et al., Polyaminocarboxylic acids with quinoxaline structure derived from o-diamines, An. Quim., Ser. B (1983), 79(3), 329–35.
N. Borthakur et al., Studies in 1, 2, 3, 4-tetrahydro-3-oxoquinoxaline-1-acetic acid: a facile oxidation of active methylene group, Indian J. Chem., Sect. B (1981), 20B(9), 822–4.
Yamamoto et al., JA–7008 422–R, (Mar. 26, 1970) 4–Acyl–3,4–dihydro–2(1H)–quinoxalinone derivatives having anti-inflammatory activity J3A.
Sumitomo Chem. Co., BE706,623 (Apr. 1, 1968) Quinoxalinones: Anti-inflammatory, Analgesic, Antipyretic.
Sankyo Co. Ltd., JA–7038639–R (Dec. 5, 1970), Suspension for Ming Tablets Prodn.
Sumitomo Chem. Co. Ltd., JA–7038700–R( Dec. 7, 1970), Novel 4–Acyl–3,4–Dihydro–2(1H) Quinoxaline Derivs Having Antinflammatory Antipyretic and Analgesic Activity.
Sankyo Co., Ltd., JA–7035800–R (Nov. 14, 1970), Coating Base Contg Polyvinylacetaldiethyl–Amino Acetate.
Takeda Chem. Ind. Ltd., JA–7035881–R (Nov. 16, 1970); Pelletization Process.
Sumitomo Chem. Co. Ltd., JA–7035903–R (Nov. 16, 1970); 4–Phenyl(or Furyl)–Alkan (or E)–Oyl–3,4Dihydro–Quinoxaline–2–Ones, Antifebrile, Anodyne.
Sumitomo Chem. Ind. Co. Ltd., JA–30509/69 (Apr. 11, 1966); (JA) as 23097/66 (Dec. 9, 1969), 4–Thienoyl–6(or 7)–Alkoxy–3,4–Dihydro–2[1H]–Quinoxalin–2–Ones Antiphlogistic, Antiferbrile, Analgesic.

Sumitomo Chem. Co. Ltd., JA–1713/69 (Apr. 8, 1966); JA as 22375/66, (Jul. 29, 1969) 4–Acyl–3,4–Dihydro–2(1H)–Quinoxalinones.
Sumitomo Chem. Co. Ltd., JA–17137/69 (Apr. 11, 1966); JA as 23396/66; (Jul 29, 1969) Preparation of 4 (Opt, p. Subst. Denzohyl)–6 or 7 Subst.3,4–Dihydro–2(1H)–Quinoxalinone, Antiinflammatory.
EP 315959A; Novel quinoxaline derivs. useful as neurotropic agents.
U.S. 3,697,545 (Oct. 10, 1972); 9–Chloro–5–methylamino–2–phenyl–4H–1,3,6–benzoxadiazocine, —antiinflammatory, anticonvulsant, and antibacterial agent.
Balzarini et al., "Resistance Pattern of Human Immunodeficiency Virus Type 1 Reverse Transcriptase to Quinoxaline S–2720," Dec. 1994, vol. 68, No. 12, pp. 7986–7992.
Balzarini et al., "Sensitivity of (138 GLU→LYS) Mutated Human Immunodeficiency Virus Type 1 (HIV–1) Reverse Transcriptase (RT) to HIV–1–Specific RT Inhibitors," Biochemical and Biophysical Research Communications, Jun. 1994, vol. 201, No. 3, pp. 1305–1312.
Elderfield, R.C., "Heterocyclic Compounds", The Quinoxalines, vol. 6, pp. 491–495, (1957).
Balzarini et al., Resistance Pattern of HIV, J. Virol., 68(12), 7986–92, 1994.
Ebbling, General Chemistry, fourth edition, pp. 991–992, 1993.
Kleim et al., Activity of a Novel Quinoxaline Derivative against HIV, Antimicrob. Agents Chemother., 37(8), 1659–64, 1993.
Kleim et al., Preclinical Evaluation of HBY 097, Antimicrob. Agents Chemother., 39(10), 2253–57, 1995.
Kleim et al., Mutational Analysis of Residue 190 of HIV, Virology, 200(2), 696–701, 1994.

*Primary Examiner*—Joseph McKane
*Attorney, Agent, or Firm*—Finnegan, Henderson, Farabow, Garrett & Dunner, L.L.P.

[57] ABSTRACT

Disclosed are quinoxalinone compounds of the formula I or Ia

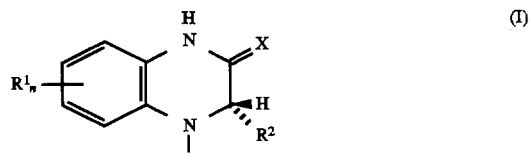

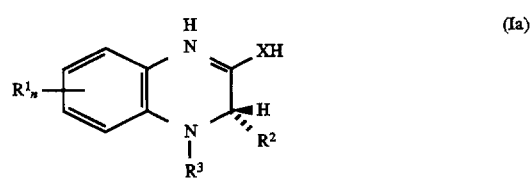

and physiologically tolerated salts and prodrugs thereof, in which n=zero, one or two;

$R^1$=fluorine, chlorine, hydroxyl or $C_1$–$C_3$-alkoxy; $R^2$=$C_1$–$C_4$-alkyl which is unsubstituted or is substituted by hydroxyl, $C_1$–$C_4$-alkoxy or $C_1$–$C_4$-alkylthio; $R^3$=$C_1$–$C_6$-alkyloxycarbonyl or $C_2$–$C_6$-alkenyloxycarbonyl, and X=oxygen, sulfur or selenium, a process for their preparation and pharmaceutical compositions containing the compounds.

11 Claims, No Drawings

QUINOXALINES, A PROCESS FOR THEIR PREPARATION AND THEIR USE

BACKGROUND OF THE INVENTION

1. Field of the Invention

The present invention relates to quinoxalines, to a process for their preparation, and to their use as virustatic agents, in particular for treating infections with the human immunodeficiency virus (HIV).

2. Description of Related Art

European Patent Application EP-509398-A describes quinoxaline derivatives for treating infections with the human immunodeficiency virus (HIV).

SUMMARY OF THE INVENTION

It has now been found, surprisingly, that a group of specially substituted quinoxalines of the formula I,

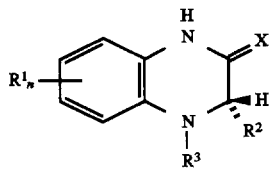

and their tautomeric forms of the formula Ia

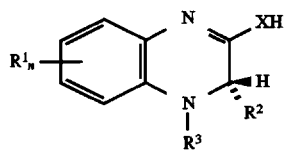

and also their physiologically tolerated salts or prodrugs exhibit an antiviral effect, in particular against retroviruses, such as, for example, human immunodeficiency virus (HIV).

In the novel compounds of the formula I or Ia:

1) n is zero, one or two, $R^1$ is fluorine, chlorine, hydroxyl or $C_1$–$C_3$-alkoxy, $R^2$ is $C_1$–$C_4$-alkyl which is optionally substituted by hydroxyl, $C_1$–$C_4$-alkoxy or $C_1$–$C_4$-alkylthio, $R^3$ is $C_1$–$C_6$-alkyloxycarbonyl or $C_2$–$C_6$-alkenyloxycarbonyl, X is oxygen, sulfur or selenium.

DESCRIPTION OF THE PREFERRED EMBODIMENTS

In a preferred group of compounds of the formula I or Ia:

2) n is zero or one, $R^1$ is fluorine, chlorine, hydroxyl or $C_1$–$C_3$-alkoxy, $R^2$ is $C_1$–$C_4$-alkyl which is optionally substituted by hydroxyl, $C_1$–$C_4$-alkoxy or $C_1$–$C_4$-alkylthio, $R^3$ is $C_1$–$C_4$-alkyloxycarbonyl or $C_2$–$C_4$-alkenyloxycarbonyl, X is oxygen or sulfur.

In another preferred group of compounds of the formula I or Ia:

3) n is zero or one, $R^1$ is fluorine, chlorine, methoxy, ethoxy or propoxy, $R^2$ is methylthiomethyl, ethyl or propyl, or $C_1$–$C_2$-alkyl which is substituted by hydroxyl or $C_1$–$C_4$-alkoxy, $R^3$ is $C_1$–$C_4$-alkyloxycarbonyl or $C_2$–$C_4$-alkenyloxycarbonyl, X is oxygen or sulfur.

Compounds of the formula I or Ia, as described above, are of very particular importance wherein the said substituents have the following meanings:

4) n is zero or one, $R^1$ is fluorine, chlorine, methoxy or ethoxy, $R^2$ is methylthiomethyl, ethyl or propyl, or $C_1$–$C_2$-alkyl which is substituted by hydroxyl or $C_1$–$C_4$-alkoxy, $R^3$ is $C_1$–$C_4$-alkyloxycarbonyl or $C_2$–$C_4$-alkenyloxycarbonyl, X is oxygen or sulfur.

The compound S-4-isopropoxycarbonyl-6-methoxy-3-(methylthiomethyl)-3,4-dihydroquinoxalin-2(1H)-thione (Ex. 85) is of very particular importance. The compounds of the formulae I and Ia possess an asymmetric carbon atom which is in the so-called S configuration.

It has now been found, surprisingly, that the novel compounds possess an antiviral effect which is markedly increased to an extent which was unexpected. It has furthermore been found that the pure enantiomers are markedly easier to dissolve than are the associated racemic compounds. The latter exist as genuine racemates, i.e. as 1:1 compounds of the two enantiomers having individual physical properties.

As a consequence of this, the pure enantiomers are markedly better absorbed following oral administration in animal experiments. This is an important prerequisite for the development of a novel pharmaceutical.

It is well known that it is of particular importance that high blood levels can be reached in order to achieve a pharmacological or chemotherapeutic effect which is as powerful as possible.

In view of the fact that it has not been possible to reach blood levels which are adequate for suppressing viral replication when using many of the virustatic agents which have potential against HIV owing to the low bioavailability of these agents following oral administration, the novel compounds represent antiviral agents of superior activity and consequently represent a therapeutic advance.

The pure enantiomers of the compounds of the formulae I and Ia can either be directly prepared by known methods, or in analogy with known methods, or else separated subsequently.

The compounds of the formulae I and Ia can be prepared by known methods or by modifications thereof (see, for example, EP-509398-A, Rodd's Chemistry of Carbon Compounds, S. Coffey, M. F. Ansell (editors); Elsevier, Amsterdam, 1989; vol. IV part IJ, pp. 301 to 311. Heterocyclic Compounds, R. C. Elderfield (editor); Wiley, New York, 1957; vol. 6, pp. 491 to 495).

The present invention furthermore relates to a process for preparing compounds of the formulae I or Ia, as explained above in 1) to 4).

The process comprises:

A) for preparing compounds of the formula I in which X is oxygen and the radicals $R^1$, $R^2$ and $R^3$ are defined as in 1) to 4), reacting a compound of the formula II,

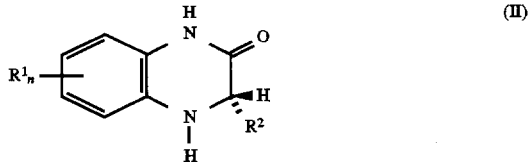

where the definitions mentioned in 1) to 4) apply to $R^1$ and $R^2$, with a compound of the formula III $$R^3\text{—}Z \qquad\qquad (III)$$

where $R^3$ has the meanings mentioned above in 1) to 4) and Z is a leaving group such as, for example, chlorine; or comprises:

B) for preparing compounds of the formula I, in which X is sulfur and $R^1$, $R^2$ and $R^3$ are defined as in 1) to 4), comprising the step of reacting a compound of the formula I, where X is oxygen and the definitions mentioned in 1) to 4) apply to $R^1$, $R^2$ and $R^3$, with a sulfurization reagent.

In the abovementioned method A), the reaction is preferably carried out using a haloformic alkyl or alkenyl ester, a dialkyl or dialkenyl carbonate or a dialkyl or alkenyl dicarbonate. The substituent Z in the formula III is accordingly a suitable leaving group such as, for example, chlorine, bromine or iodine, an alkoxy or alkenyloxy radical, or an alkoxycarbonyloxy or alkenyloxycarbonyloxy group. Z is preferably chlorine.

The reaction is expediently carried out in an inert solvent. Examples of suitable solvents are aromatic hydrocarbons, such as toluene or xylene; lower alcohols, such as methanol, ethanol or 1-butanol; ethers, such as tetrahydrofuran or glycol dimethyl ether; dipolar aprotic solvents such as N,N-dimethylformamide, N-methyl-2-pyrrolidone, acetonitrile, nitrobenzene or dimethyl sulfoxide; or mixtures of these solvents. Two-phase systems containing aqueous solutions of bases in the presence of a phase transfer catalyst, such as, for example, benzyltriethylammonium chloride, are also possible.

It can be useful for a suitable base, for example an alkali metal or alkaline earth metal carbonate or hydrogen carbonate, such as sodium carbonate, calcium carbonate or sodium bicarbonate; an alkali metal or alkaline earth metal hydroxide, such as potassium hydroxide or barium hydroxide; an alcoholate such as sodium ethoxide or potassium tert-butoxide; an organolithium compound, such as butyllithium or lithium diisopropylamide; an alkali metal or alkaline earth metal hydride, such as sodium hydride or calcium hydride; an alkali metal fluoride, such as potassium fluoride; or an organic base, such as triethylamine, pyridine, 4-methylpyridine or 4-(dimethylamino)pyridine, to be present in order to capture the acid which is liberated during the reaction.

In many cases, it is appropriate to add an iodine salt, for example potassium iodide. The reaction is usually carried out at temperatures of between −10° and 160° C., preferably at room temperature.

For this reaction, any nucleophilic substituents such as, for example, hydroxyl, mercapto or amino groups, with the exception of the 4 position in compounds of the formula II, must be derivatized in a suitable manner before carrying out the reaction or be provided with customary protective groups, which can subsequently be eliminated, such as, for example, acetyl, benzyl, trityl, tetrahydropyranyl or tert-butoxycarbonyl.

2,4-Bis(4-methoxyphenyl)-1,3-dithia-2,4-diphosphetane-2,4-disulfide (Lawesson's reagent), bis(tricyclohexyltin) sulfide, bis(tri-n-butyltin) sulfide, bis(triphenyltin) sulfide, bis(trimethylsilyl) sulfide or phosphorus pentasulfide may be preferably used as the sulfurization reagent for the reaction as described above in B).

The reaction is expediently carried out in an organic solvent or a solvent mixture, at from −10° to 120° C., preferably at from room temperature to 60° C., and as far as possible under anhydrous conditions. Examples of suitable solvents are carbon disulfide, toluene, xylene, pyridine, dichloromethane, 1,2-dichloroethane, tetrahydrofuran, ethyl acetate or butyl acetate. When using the abovementioned tin or silyl sulfides, it is expedient to carry out the sulfurization reaction in the presence of a Lewis acid such as boron trichloride.

Owing to its relatively low reactivity, the presence of a carbonyl group in the $R^3$ radical in the compounds of the formula I does not interfere in this context, so that it is possible to carry out the sulfurization selectively.

The quinoxalines of the formula II which are required as starting materials for the described syntheses are either known from the literature or can be prepared by known methods, for example using the methods described in European Patent Application EP-509398-A.

The present invention also relates to the compounds as described in 1) to 4) as pharmaceuticals which are preferably used for treating viral diseases, in particular diseases caused by HIV.

The present invention furthermore relates to pharmaceuticals which contain at least one novel compound and to the use of the said compounds for preparing pharmaceuticals, preferably for the treatment of viral diseases, in particular for the treatment of diseases which are caused by HIV.

The present invention furthermore relates to the use of compounds of the abovementioned formula I or Ia for preparing pharmaceuticals for treating viral diseases.

The compounds mentioned and explained in 1) to 4) above are preferred for this use.

The novel pharmaceuticals may be administered to a host in need thereof enterally (orally), parenterally (intravenously), rectally, subcutaneously, intramuscularly or locally (topically).

They can be administered in the form of solutions, powders (tablets and capsules, including microcapsules), ointments (creams or gels) or suppositories. Pharmaceutically acceptable carriers including customary liquid or solid fillers and extenders, solvents, emulsifiers, lubricants, taste corrigents, dyes and/or buffering substances are suitable for use as auxiliary substances for formulations of this nature.

As an expedient dosage, from 0.1 to 10, preferably from 0.2 to 8, mg are administered per kg of body weight once or several times daily. The dosage units employed expediently depend on the relevant pharmacokinetics of the substance or the pharmaceutical preparation which is used.

The dosage unit of the novel compounds which is used is, for example, from 1 to 1500 mg, preferably from 50 to 500 mg.

The novel compounds may also be administered to a host in need thereof in combination with other antiviral agents such as, for example, nucleoside analogs, protease inhibitors or adsorption inhibitors, immunostimulants, interferons, interleukins and colony-stimulating factors (e.g. GM-CSF, G-CSF and M-CSF).

Pure enantiomers are understood to mean those compounds in which the enantiomer ratio is at least 95:5, preferably at least 97:3.

The present invention is explained in more detail by the following examples and by the content of the patent claims.

EXAMPLE 1

N-(5-Fluoro-2-nitrophenyl)-S-methyl-L-cysteine 16.2 g of (−)-S-Methyl-L-cysteine (0.1 mol) are suspended in a mixture of 120 ml of water and 120 ml of acetone in a four-necked flask under $N_2$. 30.4 ml (22.2 g) of triethylamine (0.22 mol) are added rapidly while stirring. 15.9 g of 2,4-difluoronitrobenzene (0.1 mol) are added, with further stirring, to the resulting yellow solution. The mixture is heated to reflux for 7.5 hours while stirring (orange-colored solution) and the acetone is then stripped off under reduced pressure on a rotary evaporator; the aqueous residue is transferred to a separating funnel and extracted 2× with approximately 50 ml of methyl tert-butyl ether (MTB ether). This extract is composed, in the main, of 2,4-difluoronitrobenzene and is discarded. The aqueous phase is transferred to a four-necked flask and 150 ml of MTB ether are added to it, after which the mixture is adjusted, while being cooled (<25° C.), to pH 1 with approximately 25 ml of 38% sulfuric acid. The mixture is then stirred thoroughly until clear phases are formed. The ether phase is separated off and the aqueous phase is extracted once again with 50 ml of MTB ether. The extracts are dried over sodium sulfate and evaporated on a rotary evaporator. The yield comprises 27 g of a yellow oil which soon solidifies. M.p. 147° (from water/methanol).

MS: chemical ionization, $(M+H)^+=275$

| Analysis: | Calculated | Found |
|---|---|---|
| C | 43.8% | 43.8% |
| H | 4.0% | 4.1% |
| N | 10.2% | 10.0% |
| S | 11.7% | 11.3% |

EXAMPLE 2

N-(5-Methoxy-2-nitrophenyl)-S-methyl-L-cysteine 27 g of N-(5-fluoro-2-nitrophenyl)-S-methyl-L-cysteine (0.1 mol) from Example 1 are dissolved in 150 ml of absolute methanol in a four-necked flask, and 14.4 g of 95% sodium methoxide (0.25 mmol) are added in portions, within the space of 20 minutes and under argon, to this solution while stirring well and while cooling by means of an ice bath. The mixture is then heated to reflux for 2 hours while stirring. TLC monitoring then indicates that the reaction is complete.

Most of the methanol is stripped off under reduced pressure on a rotary evaporator. 200 ml of ice water are added to the residue and this mixture is adjusted to a pH of 1 with approximately 25 ml of 38% sulfuric acid and then thoroughly stirred with 150 ml of MTB ether. The ether phase is separated off and the aqueous phase is extracted once again with 30 ml of MTB ether and subjected to rotary evaporation under reduced pressure.

Yield: 21.5 g of brown-red oil which slowly crystallizes.

MS: chemical ionization, $(M+H)^+=287$

HPLC: 99.3% of S-enantiomer

| Analysis: | Calculated | Found |
|---|---|---|
| C | 46.2% | 47.3% |
| H | 4.9% | 5.6% |
| N | 9.8% | 9.1% |
| S | 11.1% | 10.6% |

EXAMPLE 3

S-6-methoxy-3-(methylthiomethyl)-3,4-dihydroquinoxalin-2(1H)-one 20.7 g of the compound from Example 2 (0.065 mol) are dissolved in 250 ml of methanol and hydrogenated under argon with 0.5 ml of glacial acetic acid and approximately 20 g of Raney nickel under standard pressure and at room temperature. The hydrogenation is complete when TLC is no longer able to detect any starting material. The mixture is filtered with suction, while being overlaid with nitrogen, and the filter residue is then washed with 100 ml of methanol.

The filter residue, including the catalyst, is thoroughly stirred, at from 45° to 50° C., with dimethylformamide (DMF), while being overlaid with nitrogen, and this mixture is then once again filtered with suction through a clarifying layer. The product-containing DMF solution is allowed to run directly into 1 l of ice water which is being stirred and to which 2 g of ascorbic acid have been added as an antioxidant. During this procedure, the product results in the form of pale yellow crystals. These are filtered off with suction, washed with approximately 2 l of water then with 500 ml of ethanol and then with 300 ml of pentane, and dried over phosphorus pentoxide.

The yield is 10.8 g; a further 1.3 g can be obtained by concentrating the filtrate.

M.p. from 186° to 187° C., yellow-grayish solid.

$^1$H-NMR (200 MHz, $d_6$-DMSO): $\delta$=2.08 (s, 3H, $SCH_3$), 2.75 ($dq_{AB}$, 2H, —$CH_2$—S), 3.65 (s, 3H, MeO), 3.95 (m, 1H, CH), 6.05 (br, s, NH), 6.1–6.7 (m, 3H, aromatics), 10.15 (s, 1H, amide).

MS: chemical ionization, $(M+H)^+=239$

HPLC: 97.5% purity, 98.2% of the S-enantiomer

Optical rotation: $[\alpha]_D^{22}=-42°$ (c=1 in acetone)

| Analysis: | Calculated | Found |
|---|---|---|
| C | 55.5% | 55.2% |
| H | 5.9% | 5.8% |
| N | 11.8% | 11.7% |
| S | 13.4% | 13.3% |

The following are obtained in an analogous manner:

EXAMPLE 4

S-6-Ethoxy-3-(methylthiomethyl)-3,4-dihydroquinoxalin-2(1H)-one

Obtained from the compound of Example 1 using lithium ethoxide in ethanol and carrying out reduction and ring closure in analogy with Example 2.

MS: chemical ionization, $(M+H)^+=253$ $^1$H-NMR (200 MHz, $d_6$-DMSO): ethoxy group $\delta$=1.27 (t, 3H), 3.87 (q, 2H)

EXAMPLE 5

S-3-(Methylthiomethyl)-6-propoxy-3,4-dihydroquinoxalin-2(1H)-one

Obtained from the compound of Example 1 using sodium propoxide in propanol.

M.p. resin, MS: chemical ionization, $(M+H)^+=267$ $^1$H-NMR (200 MHz, $d_6$-DMSO): propoxy group $\delta$=0.95 (t, 3H), 1.67 (q, 2H), 3.79 (t, 2H)

EXAMPLE 6

S-3-(Methylthiomethyl)-3,4-dihydroquinoxalin-2(1H)-one

Obtained by using 2-fluoronitrobenzene in place of 2,4-difluoronitrobenzene in Example 1.

M.p. 109° C., MS: chemical ionization, $(M+H)^+=208$

EXAMPLE 7

S-6-Fluoro-3-(methylthiomethyl)-3,4-dihydroquinoxalin-2(1H)-one

Obtained by direct further use of the compound from Example 1 in reduction and ring closure reactions as in Example 3.

M.p. 149° C., MS: chemical ionization, (M+H)⁺=243

EXAMPLE 8

S-6-Chloro-3-(methylthiomethyl)-3,4-dihydroquinoxalin-2(1H)-one

Obtained by using 2,4-dichloronitrobenzene in place of 2,4-difluoronitrobenzene in Example 1 and using sodium hydroxide and glycol monomethyl ether at reflux temperature.

M.p. 149° C., MS: chemical ionization, (M+H)⁺=243

When other amino acids are used, for example, the corresponding compounds of the formula II, in which the [lacuna] substituent of the amino acid employed becomes the substituent $R^2$ in formula II, can be obtained in an analogous manner to that described in Examples 1 to 8:

TABLE 1

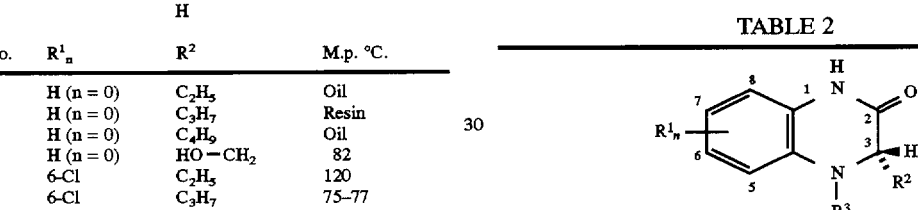

(II)

| Example No. | $R^1_n$ | $R^2$ | M.p. °C. |
|---|---|---|---|
| 9 | H (n = 0) | $C_2H_5$ | Oil |
| 10 | H (n = 0) | $C_3H_7$ | Resin |
| 11 | H (n = 0) | $C_4H_9$ | Oil |
| 12 | H (n = 0) | HO—$CH_2$ | 82 |
| 13 | 6-Cl | $C_2H_5$ | 120 |
| 14 | 6-Cl | $C_3H_7$ | 75–77 |
| 15 | 6-Cl | $C_4H_9$ | Oil |
| 16 | 6-F | $C_2H_5$ | 93 |
| 17 | 6-F | $C_3H_7$ | Resin |
| 18 | 6-F | HO—$CH_2$ | 134 |
| 19 | 6-$CH_3O$ | $C_2H_5$ | Oil |
| 20 | 6-$CH_3O$ | $C_3H_7$ | 138 |
| 21 | 6-$CH_3O$ | $C_4H_9$ | |
| 22 | 6-$CH_3O$ | HO—$CH_2$ | 125 decomp. |
| 23 | 6-$CH_3O$ | $CH_3CH(OH)$— | 156 |
| 24 | 6-$CH_3O$ | $CH_3O$—$CH_2$ | 167 |
| 25 | 6-$C_2H_5O$ | $C_2H_5$ | |
| 26 | 6-$C_2H_5O$ | $C_3H_7$ | |
| 27 | 6-$C_2H_5O$ | $CH_3O$—$CH_2$ | |
| 28 | 6-$C_3H_7O$ | $C_2H_5$ | |
| 28a | 6-OH | $CH_3SCH_2$ | 146 |

EXAMPLE 29

S-4-Isopropoxycarbonyl-6-methoxy-3-(methylthiomethyl)-3,4-dihydroquinoxalin-2(1H)-one 11.9 g (0.05 mol) of the compound from Example 3 are suspended in 300 ml of methylene chloride under nitrogen. 7.0 g of 4-methylpyridine (0.075 mol), as base, are added rapidly while stirring. 60 ml of a 1 molar solution of isopropyl chloroformate in toluene (0.06 mol) are then added dropwise at room temperature within the space of 30 minutes. During this procedure, the suspension slowly goes into solution. Monitoring by TLC indicates that the reaction is complete after from 4 to 6 hours at room temperature. The solution is acidified with 2N sulfuric acid, the organic phase is separated off, and the aqueous phase is extracted once more with 50 ml of methylene chloride. After the solvents have been evaporated off under reduced pressure, a semi-solid product remains which is recrystallized from diisopropyl ether while stirring.

Yield: 15.0 g, m.p. 115° C.

¹H-NMR (200 MHz, d₆-DMSO): δ=1.3 (2d, J=7 Hz, 6H, 2 isopropyl-$CH_3$), 2.1 (s, 3H, $SCH_3$), 2.35+2.7 (dq$_{AB}$, 2H, —$CH_2$—S), 3.73 (s, 3H, MeO), 4.87 (q, 1H, CH), 4.97 (m, J=7 Hz, 1H, isopropyl-CH), 6.7–7.25 (m, 3H, aromatics), 10.65 (s, 1H, amide).

MS: chemical ionization, (M+H)⁺=325

HPLC: 98% purity, 99.9% of S-enantiomer

Optical rotation: $[\alpha]_D^{22}$=39° (c=1 in methanol)

| Analysis: | Calculated | Found |
|---|---|---|
| C | 55.6% | 55.5% |
| H | 6.2% | 5.8% |
| N | 8.6% | 8.4% |
| S | 9.8% | 9.7% |

When, for example, compounds of the formula II, as mentioned, for example, in Examples 3–28, are used, the following compounds of the formula I in which X=O can be obtained in an analogous manner to that described in Example 29 by reaction with the corresponding compounds of the formula III:

TABLE 2

| Example No. | $R^1_n$ | $R^2$ | $R^3$ | M.p. °C. |
|---|---|---|---|---|
| 30 | H (n = 0) | $C_2H_5$ | $COOCH(CH_3)_2$ | 163 |
| 31 | H (n = 0) | $C_3H_7$ | $COOCH(CH_3)_2$ | 117 |
| 32 | H (n = 0) | $C_4H_9$ | $COOCH(CH_3)_2$ | 120 |
| 33 | H (n = 0) | HO—$CH_2$ | $COOCH(CH_3)_2$ | |
| 34 | H (n = 0) | $CH_3SCH_2$ | $COOCH(CH_3)_2$ | 119 |
| 35 | 6-Cl | $C_2H_5$ | $COOCH(CH_3)_2$ | 145–147 |
| 36 | 6-Cl | $C_3H_7$ | $COOCH(CH_3)_2$ | |
| 37 | 6-Cl | $C_4H_9$ | $COOCH(CH_3)_2$ | |
| 38 | 6-Cl | $CH_3SCH_2$ | $COOCH(CH_3)_2$ | 105 |
| 39 | 6-F | $C_2H_5$ | $COOCH(CH_3)_2$ | 123–125 |
| 40 | 6-F | $C_3H_7$ | $COOCH(CH_3)_2$ | 110 |
| 41 | 6-F | $C_4H_9$ | $COOCH(CH_3)_2$ | |
| 42 | 6-F | $CH_3SCH_2$ | $COOCH(CH_3)_2$ | 136 |
| 43 | 6-$CH_3O$ | $C_2H_5$ | $COOCH(CH_3)_2$ | Oil |
| 44 | 6-$CH_3O$ | $C_3H_7$ | $COOCH(CH_3)_2$ | 153 |
| 45 | 6-$CH_3O$ | $C_4H_9$ | $COOCH(CH_3)_2$ | |
| 46 | 6-$CH_3O$ | HO—$CH_2$ | $COOCH(CH_3)_2$ | Resin |
| 47 | 6-$CH_3O$ | $CH_3CH(OH)$— | $COOCH(CH_3)_2$ | Resin |
| 48 | 6-$CH_3O$ | $CH_3O$—$CH_2$ | $COOCH(CH_3)_2$ | 98 |
| 49 | 6-$C_2H_5O$ | $C_2H_5$ | $COOCH(CH_3)_2$ | |
| 50 | 6-$C_2H_5O$ | $C_3H_7$ | $COOCH(CH_3)_2$ | |
| 51 | 6-$C_2H_5O$ | $CH_3O$—$CH_2$ | $COOCH(CH_3)_2$ | |
| 52 | 6-$C_2H_5O$ | $CH_3SCH_2$ | $COOCH(CH_3)_2$ | 112 |
| 53 | 6-$C_3H_7O$ | $C_2H_5$ | $COOCH(CH_3)_2$ | |
| 54 | 6-$C_3H_7O$ | $CH_3SCH_2$ | $COOCH(CH_3)_2$ | 105 |
| 55 | H (n = 0) | $C_2H_5$ | $COOC(CH_3)=CH_2$ | |
| 56 | H (n = 0) | $CH_3SCH_2$ | $COOC(CH_3)=CH_2$ | |
| 57 | 6-Cl | $C_2H_5$ | $COOC(CH_3)=CH_2$ | 143 |
| 58 | 6-Cl | $C_2H_5$ | $COOCH_2CH=CH_2$ | 122–124 |
| 59 | 6-Cl | $CH_3SCH_2$ | $COOC(CH_3)=CH_2$ | 182 |
| 60 | 6-Cl | $CH_3SCH_2$ | $COOC_3H_7$ | 68 |
| 61 | 6-Cl | $CH_3SCH_2$ | $COOC_2H_5$ | 143 |

TABLE 2-continued

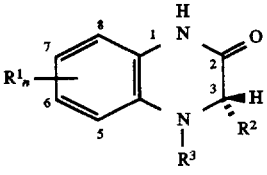

| Example No. | $R^1_n$ | $R^2$ | $R^3$ | M.p. °C. |
|---|---|---|---|---|
| 62 | 6-F | $C_2H_5$ | $COOC(CH_3)=CH_2$ | 125 |
| 63 | 6-F | $C_3H_7$ | $COOC(CH_3)=CH_2$ | |
| 64 | 6-F | $CH_3SCH_2$ | $COOC(CH_3)=CH_2$ | |
| 65 | 6-$CH_3O$ | $C_2H_5$ | $COOC(CH_3)=CH_2$ | |
| 66 | 6-$CH_3O$ | $C_3H_7$ | $COOC(CH_3)=CH_2$ | |
| 67 | 6-$CH_3O$ | $CH_3O-CH_2$ | $COOC(CH_3)=CH_2$ | |
| 68 | 6-$CH_3O$ | $CH_3SCH_2$ | $COOC(CH_3)=CH_2$ | 152 |
| 69 | 6-$CH_3O$ | $CH_3SCH_2$ | $COOCH_2CH(CH_3)-C_2H_5$ | |
| 70 | 6-$C_2H_5O$ | $C_2H_5$ | $COOC(CH_3)=CH_2$ | |
| 71 | 6-$C_2H_5O$ | $C_3H_7$ | $COOC(CH_3)=CH_2$ | |
| 72 | 6-$C_2H_5O$ | $CH_3O-CH_2$ | $COOC(CH_3)=CH_2$ | |
| 73 | 6-$C_2H_5O$ | $CH_3SCH_2$ | $COOC(CH_3)=CH_2$ | |
| 74 | H (n = 0) | $C_2H_5$ | $COOC_2H_5$ | |
| 75 | H (n = 0) | $C_3H_7$ | $COOC_2H_5$ | |
| 76 | H (n = 0) | $CH_3SCH_2$ | $COOC_2H_5$ | |
| 77 | 6-Cl | $C_2H_5$ | $COOC_2H_5$ | |
| 78 | 6-F | $C_2H_5$ | $COOC_2H_5$ | 116 |
| 79 | 6-F | $CH_3SCH_2$ | $COOC_2H_5$ | |
| 80 | 6-$CH_3O$ | $C_2H_5$ | $COOC_2H_5$ | |
| 81 | 6-$CH_3O$ | $CH_3O-CH_2$ | $COOC_2H_5$ | |
| 82 | 6-$CH_3O$ | $CH_3SCH_2$ | $COOC_2H_5$ | |
| 83 | 6-$C_2H_5O$ | $C_2H_5$ | $COOC_2H_5$ | |
| 84 | 6-$C_2H_5O$ | $CH_3SCH_2$ | $COOC_2H_5$ | |
| 84a | 6-OH | $CH_3SCH_2$ | $COOCH(CH_3)_2$ | 182 |
| 84b | 6-OH | $C_2H_5$ | $COOCH(CH_3)_2$ | 201 |
| 84c | 6-Cl | $CH_3$ | $COOC_2H_5$ | 151 |
| 84d | 6-Cl | $C_4H_9$ | $COOC(CH_3)=CH_2$ | 158 |
| 84e | 6-Cl | $CH_3SCH_2$ | $COOC_2H_5$ | 143 |
| 84f | 6-Cl | $CH_3SCH_2$ | $COOC_3H_7$ | 68 |
| 84g | 6-$CH_3O$ | $CH_3SCH_2$ | $COOCH(CH_3)-C_2H_5$ | 86 |
| 84h | 6-$CH_3O$ | $CH_3SCH_2$ | $COOCH_2CH(CH_3)_2$ | 60 |
| 84i | 6-F | $CH_3$ | $COOCH(CH_3)_2$ | 151 |
| 84j | 6-F | $C_2H_5$ | $COOCH(CH_3)-C_2H_5$ | Resin |
| 84k | 6-F | $C_2H_5$ | $COOCH_3$ | 50 |
| 84l | 6-F | $C_2H_5$ | $COOC_4H_9$ | 92 |
| 84m | 6-F | $C_2H_5$ | $COOCH_2CH(CH_3)_2$ | 90 |
| 84n | 6-F | $CH_2OH$ | $COOCH(CH_3)_2$ | Resin |
| 84o | 6-F | $CH_3OCH_2$ | $COOCH(CH_3)_2$ | 114 |

EXAMPLE 85

S-4-Isopropoxycarbonyl-6-methoxy-3-(methylthiomethyl)-3,4-dihydroquinoxalin-2(1H)-thione 16.1 g of the compound from Example 29 (0.05 mol) are dissolved in 200 ml of dry dimethoxyethane, and 13 g of finely powdered phosphorus pentasulfide (0.06 mol) are added to this solution, under argon and while stirring, and the mixture is then stirred at room temperature. After 24 hours, the reaction is still not complete so that a further 4 g of phosphorus pentasulfide are added. After having been incubated at room temperature for 24 hours, the mixture is stirred for a further 3 hours at 30° C. The mixture is then filtered with suction through a clarifying layer in order to separate off solids, which are then washed with dimethoxyethane. The collected filtrates are evaporated under reduced pressure. The dark oil which remains is taken up in 250 ml of MTB ether and this solution is thoroughly stirred with 200 ml of a saturated solution of sodium hydrogen carbonate. The phases are separated and the aqueous phase is extracted once again with 20 ml of MTB ether. The organic extracts are dried over magnesium sulfate or sodium sulfate and subjected to rotary evaporation.

The yellow-brown oil which remains is dissolved in 30 ml of hot diisopropyl ether. It crystallizes out when the solution is cooled while being stirred. The crystals which have precipitated are washed with a little diisopropyl ether and n-pentane and dried in a desiccator.

Yield 91.4 g, m.p. 103° C.

$^1$H-NMR (200 MHz, $d_6$-DMSO): δ=1.27 (2d, J=7 Hz, 6H, 2 isopropyl-$CH_3$), 2.1 (s, 3H, $SCH_3$), 2.34+2.79 ($dq_{AB}$, 2H, —$CH_2$—S), 3.75 (s, 3H, MeO), 4.97 (m, J=7 Hz, 1H, isopropyl-CH), 5.25 (q, 1H, CH), 6.75–7.3 (m, 3H, aromatics), 12.73 (s, 1H, thioamide).

MS: chemical ionization, (M+H)$^+$=341

HPLC: 99.6% purity, 99.4% of S-enantiomer

Optical rotation: $[\alpha]_D^{22}$ =18° (c=1 in methanol)

| Analysis: | Calculated | Found |
|---|---|---|
| C | 52.9% | 52.9% |
| H | 5.9% | 5.3% |
| N | 8.4% | 8.3% |
| S | 18.8% | 18.6% |

When, for example, compounds of the formula I in which X=O, as mentioned, for example, in Examples 30 to 84, are used, the following compounds of the formula I in which X=S can be obtained in an analogous manner to that described in Example 85 by reaction with the corresponding sulfurization reagents:

TABLE 3

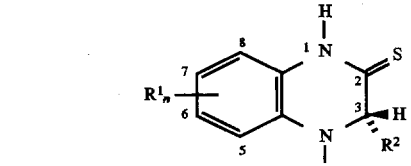

| Example No. | $R^1_n$ | $R^2$ | $R^3$ | M.p. °C. |
|---|---|---|---|---|
| 86 | H (n = 0) | $C_2H_5$ | $COOCH(CH_3)_2$ | 114 |
| 87 | H (n = 0) | $C_3H_7$ | $COOCH(CH_3)_2$ | 128 |
| 88 | H (n = 0) | $C_4H_9$ | $COOCH(CH_3)_2$ | 78 |
| 89 | H (n = 0) | $HO-CH_2$ | $COOCH(CH_3)_2$ | |
| 90 | H (n = 0) | $CH_3SCH_2$ | $COOCH(CH_3)_2$ | Oil |
| 91 | 6-Cl | $C_2H_5$ | $COOCH(CH_3)_2$ | 161 |
| 92 | 6-Cl | $C_3H_7$ | $COOCH(CH_3)_2$ | |
| 93 | 6-Cl | $C_4H_9$ | $COOCH(CH_3)_2$ | |
| 94 | 6-Cl | $CH_3SCH_2$ | $COOCH(CH_3)_2$ | 124 |
| 95 | 6-F | $C_2H_5$ | $COOCH(CH_3)_2$ | 93 |
| 96 | 6-F | $C_3H_7$ | $COOCH(CH_3)_2$ | 60 |
| 97 | 6-F | $C_4H_9$ | $COOCH(CH_3)_2$ | |
| 98 | 6-F | $CH_3SCH_2$ | $COOCH(CH_3)_2$ | 122 |
| 99 | 6-$CH_3O$ | $C_2H_5$ | $COOCH(CH_3)_2$ | 74 |
| 100 | 6-$CH_3O$ | $C_3H_7$ | $COOCH(CH_3)_2$ | 140 |
| 101 | 6-$CH_3O$ | $C_4H_9$ | $COOCH(CH_3)_2$ | |
| 102 | 6-$CH_3O$ | $HO-CH_2$ | $COOCH(CH_3)_2$ | |
| 103 | 6-$CH_3O$ | $CH_3CH(OH)-$ | $COOCH(CH_3)_2$ | |
| 104 | 6-$CH_3O$ | $CH_3O-CH_2$ | $COOCH(CH_3)_2$ | 137 |
| 105 | 6-$C_2H_5O$ | $C_2H_5$ | $COOCH(CH_3)_2$ | |
| 106 | 6-$C_2H_5O$ | $C_3H_7$ | $COOCH(CH_3)_2$ | |
| 107 | 6-$C_2H_5O$ | $CH_3O-CH_2$ | $COOCH(CH_3)_2$ | |
| 108 | 6-$C_2H_5O$ | $CH_3SCH_2$ | $COOCH(CH_3)_2$ | Oil |
| 109 | 6-$C_3H_7O$ | $C_2H_5$ | $COOCH(CH_3)_2$ | |
| 110 | 6-$C_3H_7O$ | $CH_3SCH_2$ | $COOCH(CH_3)_2$ | Resin |
| 111 | H (n = 0) | $C_2H_5$ | $COOC(CH_3)=CH_2$ | |

TABLE 3-continued

Structure: benzene ring with positions labeled (1-N-H at position 1, 2=S, 3-H with R² substituent, N-R³ at position 4, positions 5,6,7,8 on ring, R¹ₙ substituent)

| Example No. | R¹ₙ | R² | R³ | M.p. °C. |
|---|---|---|---|---|
| 112 | H (n = 0) | CH₃SCH₂ | COOC(CH₃)=CH₂ | |
| 113 | 6-Cl | C₂H₅ | COOC(CH₃)=CH₂ | 170 |
| 114 | 6-Cl | C₂H₅ | COOCH₂CH=CH₂ | 123 |
| 115 | 6-Cl | CH₃SCH₂ | COOC(CH₃)=CH₂ | 128 |
| 116 | 6-Cl | CH₃SCH₂ | COOC₃H₇ | |
| 117 | 6-Cl | CH₃SCH₂ | COOC₂H₅ | |
| 118 | 6-F | C₂H₅ | COOC(CH₃)=CH₂ | |
| 119 | 6-F | C₃H₇ | COOC(CH₃)=CH₂ | |
| 120 | 6-F | CH₃SCH₂ | COOC(CH₃)=CH₂ | |
| 121 | 6-CH₃O | C₂H₅ | COOC(CH₃)=CH₂ | |
| 122 | 6-CH₃O | C₃H₇ | COOC(CH₃)=CH₂ | |
| 123 | 6-CH₃O | CH₃O—CH₂ | COOC(CH₃)=CH₂ | |
| 124 | 6-CH₃O | CH₃SCH₂ | COOC(CH₃)=CH₂ | 152 |
| 125 | 6-CH₃O | CH₃SCH₂ | COOCH₂CH(CH₃)—C₂H₅ | |
| 126 | 6-C₂H₅O | C₂H₅ | COOC(CH₃)=CH₂ | |
| 127 | 6-C₂H₅O | C₃H₇ | COOC(CH₃)=CH₂ | |
| 128 | 6-C₂H₅O | CH₃O—CH₂ | COOC(CH₃)=CH₂ | |
| 129 | 6-C₂H₅O | CH₃SCH₂ | COOC(CH₃)=CH₂ | |
| 130 | H (n = 0) | C₂H₅ | COOC₂H₅ | |
| 131 | H (n = 0) | C₃H₇ | COOC₂H₅ | |
| 132 | H (n = 0) | CH₃SCH₂ | COOC₂H₅ | |
| 133 | 6-Cl | C₂H₅ | COOC₂H₅ | |
| 134 | 6-F | C₂H₅ | COOC₂H₅ | Resin |
| 135 | 6-F | CH₃SCH₂ | COOC₂H₅ | |
| 136 | 6-CH₃O | C₂H₅ | COOC₂H₅ | |
| 137 | 6-CH₃O | CH₃O—CH₂ | COOC₂H₅ | |
| 138 | 6-CH₃O | CH₃SCH₂ | COOC₂H₅ | |
| 139 | 6-C₂H₅O | C₂H₅ | COOC₂H₅ | |
| 140 | 6-C₂H₅O | CH₃SCH₂ | COOC₂H₅ | |
| 140a | 6-OH | CH₃SCH₂ | COOCH(CH₃)₂ | 113 |
| 140b | 6-OH | C₂H₅ | COOCH(CH₃)₂ | Resin |
| 140c | 6-Cl | CH₃ | COOCH₂CH=CH₂ | 144 |
| 140d | 6-Cl | CH₃ | COOC(CH₃)=CH₂ | 149 |
| 140e | 6-Cl | C₄H₉ | COOC(CH₃)=CH₂ | 132 |
| 140f | 6-CH₃O | CH₃SCH₂ | COOCH(CH₃)—C₂H₅ | 60 |
| 140g | 6-CH₃O | CH₃SCH₂ | COOCH₂CH(CH₃)₂ | 89 |
| 140h | 6-F | C₂H₅ | COOCH₃ | 146 |
| 140i | 6-F | C₂H₅ | COOC₄H₉ | 103 |
| 140j | 6-F | C₂H₅ | COOCH₂CH(CH₃)₂ | Resin |
| 140k | 6-F | C₂H₅ | COOCH(CH₃)—C₂H₅ | 51 |
| 140l | 6-F | CH₃OCH₂ | COOCH(CH₃)₂ | 143 |

Activity tests

Testing of preparations against HIV in cell culture

Description of the method:
 medium: RMPI, pH 6.8

Complete medium additionally contains 20% fetal calf serum and 40 IU/ml recombinant interleukin 2.

Cells

Lymphocytes, which have been isolated from fresh donor blood by means of Ficoll® gradient centrifugation, are cultured, for 36 hours at 37° C. and under 5% $CO_2$, in complete medium which additionally contains 2 g/ml phytohemagglutinin (Wellcome). After 10% DMSO has been added, the cells are frozen at a cell density of $5\times10^6$ and stored in liquid nitrogen. For the experiment, the cells are thawed, washed in the RPMI medium and cultured for 3 to 4 days in the complete medium.

Assay mixture

The test preparations were dissolved in DMSO at a concentration of 16.7 mg/ml, and these solutions were diluted with complete medium to a concentration of 1 mg/ml. 0.4 ml of medium was initially introduced into 24-well multiwell plates. After 0.1 ml of the dissolved preparation had been added to the upper row of the plate, a geometric dilution series was produced by transferring 0.1 ml on each occasion. Preparation-free controls contained 0.4 ml of complete medium containing 0.5% DMSO.

Lymphocyte cultures having a cell count of $5\times10^5$ cells/ml were infected by adding a 1/50 volume of the supernatant from HIV-infected lymphocyte cultures. The titer of these culture supernatants was determined by end-point dilution to be $1-5\times10^6$ infectious units/ml. After having been incubated at 37° C. for 30 min, the infected lymphocytes were centrifuged off and taken up once again in the same volume of medium. 0.6 ml of this cell suspension was added to each of the wells in the test plate. The assay mixtures were incubated at 37° C. for 3 days.

Evaluation

The infected cell cultures were examined under the microscope for the presence of giant cells, which are indicative of active viral replication in the culture. The lowest preparation concentration at which no giant cells occurred was determined and taken to be the inhibitory concentration against HIV. As a control, the supernatants from the culture plates were assayed for the presence of HIV antigen using an HIV antigen test in accordance with the manufacturer's (Organon) instructions.

Results

TABLE 4

| Compound from Example No. | T-cell culture assay MIC $EC_{50}$ (ng/ml) |
|---|---|
| 29 | <8 |
| 30 | <40 |
| 31 | 50 |
| 34 | <1 |
| 35 | <80 |
| 38 | <1 |
| 39 | 8 |
| 40 | 80 |
| 42 | <8 |
| 43 | <1 |
| 44 | <80 |
| 52 | <8 |
| 54 | 40 |
| 57 | 1 |
| 58 | 10 |
| 59 | 20 |
| 60 | 40 |
| 61 | 2 |
| 62 | 80 |
| 68 | 8 |
| 78 | <80 |
| 84i | 80 |
| 84j | <80 |
| 84l | 80 |
| 84o | 80 |
| 85 | 2 |
| 86 | 1 |
| 87 | 4 |
| 88 | <40 |
| 90 | <8 |
| 91 | 2 |
| 94 | <8 |
| 95 | 2 |
| 96 | 80 |
| 98 | 3 |
| 99 | <1 |
| 100 | 4 |
| 104 | 8 |
| 108 | <5 |
| 110 | 4 |
| 113 | 0.8 |

TABLE 4-continued

| Compound from Example No. | T-cell culture assay MIC $EC_{50}$ (ng/ml) |
|---|---|
| 114 | 1.6 |
| 115 | 1.6 |
| 124 | <8 |
| 134 | 8 |
| 140a | 40 |
| 140b | <80 |
| 140c | 40 |
| 140d | 10 |
| 140f | 8 |
| 140g | 40 |
| 140h | 10 |
| 140i | 10 |
| 140j | 10 |
| 140k | 8 |
| 140l | 8 |

Examination of the substances for their ability to inhibit HIV reverse transcriptase The activity of the reverse transcriptase (RT) was determined using a scintillation proximity assay (SPA).

The reagent kit for the RT SPA was obtained from Amersham/Buchler (Braunschweig). The RT enzyme (derived from HIV and cloned in E. coli) was obtained from HT Biotechnology Ltd., Cambridge, UK.

Assay mixture

The test was carried out in accordance with the manufacturer's (Amersham) methods manual, with the following modifications:

Bovine serum albumin was added to the assay buffer to a final concentration of 0.5 mg/ml.

The test was carried out in Eppendorf tubes using an assay mixture volume of 100 µl.

The manufacturer's RT concentrate (5000 U/ml) was diluted to an activity of 15 U per ml using 20 mM tris-HCl buffer, pH 7.2, 30% glycerol.

The assay mixtures were incubated for 60 min (37° C.).

After the reaction had been stopped and "developed" with the bead suspension, 130 µl of assay mixture were transferred into 4.5 ml of 10 mM tris-HCl buffer, pH 7.4, 0.15M NaCl and the tritium activity was measured in a β-counter.

Testing the substances

In order to carry out a preliminary test of their inhibitory activity, the substances were dissolved in DMSO (stock solution, c=1 mg/ml) and tested when diluted $10^{-1}$, $10^{-2}$, $10^{-3}$ etc. in DMSO.

In order to determine $IC_{50}$ values, the stock solutions of inhibitor were further diluted in 50 mM tris-HCl buffer, pH 8, and tested at suitable concentrations.

The concentration associated with 50% inhibition of the enzyme was ascertained from the plot of RT activity against log $C_{inh}$.

The results of the investigation are shown in Table 5.

TABLE 5

| Compound from Example No. | Reverse transcriptase assay $IC_{50}$ (ng/ml) |
|---|---|
| 29 | 10–100 |
| 34 | 10–100 |
| 35 | 10 |
| 38 | 5 |
| 39 | 20 |
| 40 | 10–100 |
| 52 | 10–100 |
| 57 | 10–100 |
| 58 | 10–100 |
| 59 | 18 |
| 60 | 10 |
| 61 | 10–100 |
| 62 | 92 |
| 68 | 16 |
| 78 | 80 |
| 84g | 118 |
| 84i | 170 |
| 84j | 87 |
| 84l | 150 |
| 85 | 8 |
| 86 | 11 |
| 87 | 27 |
| 90 | 5 |
| 91 | 4 |
| 94 | 15 |
| 96 | 16 |
| 98 | 12 |
| 99 | 11 |
| 100 | 16 |
| 104 | 35 |
| 108 | 8 |
| 110 | 10–100 |
| 113 | 6 |
| 114 | 7 |
| 115 | 10 |
| 125 | 15 |
| 134 | 3 |
| 140a | 93 |
| 140b | 70 |
| 140c | 110 |
| 140d | 27 |
| 140f | 19 |
| 140g | 17 |
| 140h | 8 |
| 140i | 22 |
| 140j | 15 |
| 140k | 16 |
| 140l | 22 |

What is claimed is:

1. A compound of the formula I or Ia,

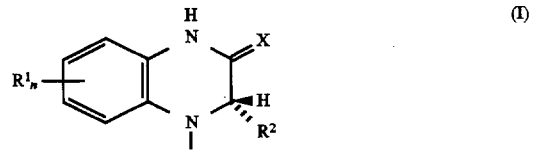

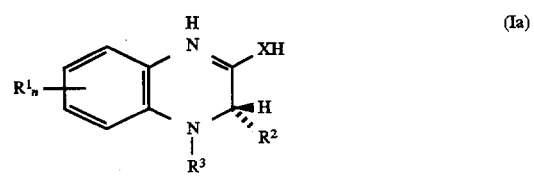

or a physiologically tolerated salt thereof, wherein, in formulae I and Ia:

n is zero, one or two, $R^1$ is fluorine, chlorine, hydroxyl or $C_1$–$C_3$-alkoxy, $R^2$ is $C_1$–$C_4$-alkyl which is unsubstituted or is substituted by hydroxyl, $C_1$–$C_4$-alkoxy or $C_1$–$C_4$-alkylthio, $R^3$ is $C_1$–$C_6$-alkyloxycarbonyl or $C_2$–$C_6$-alkenyloxycarbonyl, and X is oxygen, sulfur or selenium.

2. A compound of the formula I or Ia as claimed in claim 1, wherein the substituents in the said formulae have the following meanings:

n is zero or one, $R^1$ is fluorine, chlorine, hydroxyl or $C_1$–$C_3$-alkoxy, $R^2$ is $C_1$–$C_4$-alkyl which is unsubstituted or is substituted by hydroxyl, $C_1$–$C_4$-alkoxy or $C_1$–$C_4$-alkylthio, $R^3$ is $C_1$–$C_4$-alkyloxycarbonyl or $C_2$–$C_4$-alkenyloxycarbonyl, and X is oxygen or sulfur.

3. A compound of the formula I or Ia as claimed in claim 1, wherein the substituents in the said formulae have the following meanings:

n is zero or one, $R^1$ is fluorine, chlorine, methoxy, ethoxy or propoxy, $R^2$ is methylthiomethyl, ethyl or propyl, or $C_1$–$C_2$-alkyl which is substituted by hydroxyl or $C_1$–$C_4$-alkoxy, $R^3$ is $C_1$–$C_4$-alkyloxycarbonyl or $C_2$–$C_4$-alkenyloxycarbonyl, and X is oxygen or sulfur.

4. A compound of the formula I or Ia as claimed in claim 1, wherein the substituents in the said formulae have the following meanings:

n is zero or one, $R^1$ is fluorine, chlorine, methoxy or ethoxy, $R^2$ is methylthiomethyl, ethyl or propyl, or $C_1$–$C_2$-alkyl which is substituted by hydroxyl or $C_1$–$C_4$-alkoxy, $R^3$ is $C_1$–$C_4$-alkyloxycarbonyl or $C_2$–$C_4$-alkenyloxycarbonyl, and X is oxygen or sulfur.

5. A process for preparing a compound of the formula I or Ia

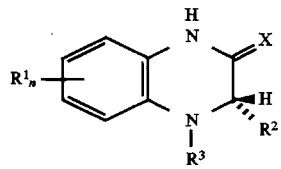
(I)

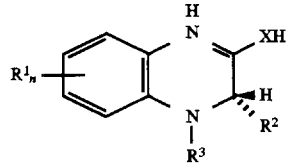
(Ia)

wherein, in formulae I and Ia:

n is zero, one or two, $R^1$ is fluorine, chlorine, hydroxyl or $C_1$–$C_3$-alkoxy, $R^2$ is $C_1$–$C_4$-alkyl which is unsubstituted or substituted by hydroxyl, $C_1$–$C_4$-alkoxy or $C_1$–$C_4$-alkylthio, $R^3$ is $C_1$–$C_6$-alkyloxycarbonyl or $C_2$–$C_6$-alkenyloxycarbonyl, and X is oxygen;

which comprises the step of reacting a compound of the formula II,

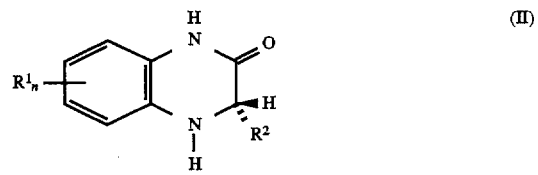
(II)

defined as above, with a compound of the formula III,

$R^3$—Z    (III)

wherein $R^3$ is defined as above and Z is a leaving group.

6. The process of claim 5, wherein Z is chlorine.

7. The process of claim 5, additionally comprising the step of reacting a compound of the formula I or Ia with a sulfurization reagent.

8. A pharmaceutical composition for the treatment of viral diseases which comprises an effective amount of a compound of the formula I or Ia as claimed in claim 1, or a physiologically tolerated salt thereof together with a pharmaceutically acceptable carrier.

9. A pharmaceutical composition which contains an effective quantity of at least one compound of the formula I or Ia as claimed in claim 1 or a physiologically tolerated salt thereof, together with a pharmaceutically acceptable carrier.

10. A method for the treatment of human immunodeficiency disease which comprises administering to a host in need of such treatment a pharmaceutical composition as claimed in claim 9.

11. A method for the treatment of human immunodeficiency disease which comprises administering to a host in need of such treatment an effective amount of a compound as claimed in claim 1.

* * * * *

UNITED STATES PATENT AND TRADEMARK OFFICE
CERTIFICATE OF CORRECTION

PATENT NO. : 5,723,461
DATED : March 3, 1998
INVENTOR(S) : Rösner et al.

It is certified that error appears in the above-identified patent and that said Letters Patent is hereby corrected as shown below:

Claim 1, column 14, lines 53-59; claim 5, column 15, lines 45-50; and title page, item [57], in the Abstract,
formula (Ia)

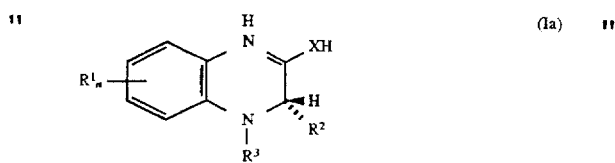

should read

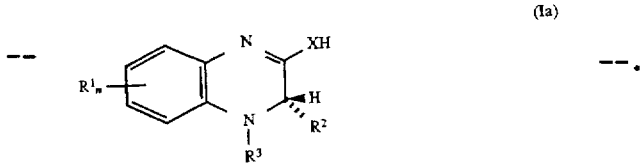

Claim 5, column 16, line 22, before "defined", insert --wherein $R^1$ and $R^2$ are--.

Signed and Sealed this

Fifteenth Day of June, 1999

Attest:

Q. TODD DICKINSON

Attesting Officer   Acting Commissioner of Patents and Trademarks